United States Patent
Fan et al.

(10) Patent No.: US 11,638,573 B2
(45) Date of Patent: *May 2, 2023

(54) PULSE OFFSET ULTRASONIC IMAGING

(71) Applicant: Shenzhen Mindray Bio-Medical Electronics Co., Ltd., Shenzhen (CN)

(72) Inventors: Rui Fan, Shenzhen (CN); Shuangshuang Li, Shenzhen (CN); Yong Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 760 days.

This patent is subject to a terminal disclaimer.

(21) Appl. No.: 16/715,957

(22) Filed: Dec. 16, 2019

(65) Prior Publication Data

US 2020/0121290 A1 Apr. 23, 2020

Related U.S. Application Data

(63) Continuation of application No. 14/258,960, filed on Apr. 22, 2014, now Pat. No. 10,524,766, which is a (Continued)

(30) Foreign Application Priority Data

May 25, 2009 (CN) .......................... 200910133494.X

(51) Int. Cl.
*A61B 8/00* (2006.01)
*A61B 8/08* (2006.01)
(Continued)

(52) U.S. Cl.
CPC .............. *A61B 8/5207* (2013.01); *A61B 8/08* (2013.01); *A61B 8/14* (2013.01); *G01S 7/52038* (2013.01);
(Continued)

(58) Field of Classification Search
CPC .................................................... G01S 7/52038
See application file for complete search history.

(56) References Cited

U.S. PATENT DOCUMENTS

| 4,809,184 A | 2/1989 | O'Donnell et al. |
| 5,454,372 A | 10/1995 | Banjanin et al. |

(Continued)

FOREIGN PATENT DOCUMENTS

| CN | 1498599 A | 5/2004 |
| CN | 1682664 A | 10/2005 |

(Continued)

OTHER PUBLICATIONS

Office Action dated Jul. 25, 2012 for U.S. Appl. No. 12/786,077, filed May 24, 2010.

(Continued)

*Primary Examiner* — Luther Behringer
(74) *Attorney, Agent, or Firm* — Kory D. Christensen

(57) ABSTRACT

A diagnostic ultrasound image of a region of interest (ROI) of a body is formed by transmitting into the ROI at least a first and a second ultrasound pulse, in which the second pulse is phase-shifted relative to the first pulse by an amount other than 0 or a multiple of 180 degrees. Discretized receive signals from the pulses are interleaved to form a resultant operating signal that is detected and beamformed as the operating signal.

10 Claims, 9 Drawing Sheets

Related U.S. Application Data continuation of application No. 12/786,077, filed on May 24, 2010, now Pat. No. 8,702,610.

(51) Int. Cl.
*G01S 7/52* (2006.01)
*A61B 8/14* (2006.01)
*G01S 15/89* (2006.01)
*G01S 15/10* (2006.01)

(52) U.S. Cl.
CPC ...... *G01S 7/52046* (2013.01); *G01S 15/8959* (2013.01); *G01S 15/108* (2013.01)

(56) References Cited

U.S. PATENT DOCUMENTS

| | | |
|---|---|---|
| 5,632,277 A | 5/1997 | Chapman et al. |
| 5,951,478 A | 9/1999 | Hwang et al. |
| 6,186,950 B1 | 2/2001 | Averkiou et al. |
| 6,206,833 B1 | 3/2001 | Christopher |
| 6,213,947 B1 | 4/2001 | Phillips |
| 6,221,018 B1 | 4/2001 | Bradley |
| 6,494,841 B1 | 12/2002 | Thomas et al. |
| 6,497,664 B1 | 12/2002 | Randall et al. |
| 6,514,209 B1 | 2/2003 | Basude et al. |
| 6,599,245 B1 | 7/2003 | Ma et al. |
| 6,866,631 B2 | 3/2005 | McLaughlin et al. |
| 7,004,905 B2 | 2/2006 | Christopher |
| 7,104,956 B1 | 9/2006 | Christopher |
| 7,513,870 B2 | 4/2009 | Christopher |
| 8,702,610 B2 | 4/2014 | Fan et al. |
| 2001/0051771 A1 | 12/2001 | Bradley et al. |
| 2002/0188199 A1 | 12/2002 | McLaughlin et al. |
| 2007/0282200 A1 | 12/2007 | Johnson et al. |
| 2008/0112265 A1 | 5/2008 | Urbano et al. |
| 2008/0114255 A1 | 5/2008 | Schwartz et al. |
| 2008/0130413 A1 | 6/2008 | Bachelor et al. |
| 2008/0200815 A1* | 8/2008 | Van Der Steen ...... A61B 8/481 600/467 |
| 2008/0234580 A1 | 9/2008 | Bruce et al. |
| 2009/0124203 A1 | 5/2009 | Song et al. |

FOREIGN PATENT DOCUMENTS

| | | |
|---|---|---|
| CN | 1976635 A | 6/2007 |
| CN | 101119767 A | 2/2008 |
| CN | 101357068 A | 2/2009 |

OTHER PUBLICATIONS

Office Action dated Feb. 21, 2013 for U.S. Appl. No. 12/786,077, filed May 24, 2010.

Office Action dated Nov. 6, 2013 for U.S. Appl. No. 12/786,077, filed May 24, 2010.

Notice of Allowance dated Jan. 30, 2014 for U.S. Appl. No. 12/786,077, filed May 24, 2010.

* cited by examiner

PULSE OFFSET ULTRASONIC IMAGING

CROSS-REFERENCE TO RELATED APPLICATIONS

This application claims priority of Chinese patent application no. 200910133494.X, filed 25 May 2009.

TECHNICAL FIELD

The invention relates to diagnostic medical ultrasonic imaging.

BACKGROUND ART

Ultrasonic imaging is a well-known diagnostic medical technique that can generate a visible image of a region of interest (ROI) by transmitting ultrasound into a patient's body, and then receiving and processing reflected ultrasonic echoes, whose characteristics carry information about the insonified body tissues.

In a conventional ultrasonic imaging system, a transmit circuit energizes an array of piezoelectric elements to generate ultrasonic transmit pulses along focused beams into the ROI of the body. Many body tissues of interest are typically nonlinear media such that non-linear distortion is created as the ultrasonic pulses propagate through them. The nature of this distortion indicates characteristics of the tissues that can be extracted for display.

There is a continual effort to improve the quality of these diagnostic images, with "quality" being defined in several different ways. As with many other forms of signal processing, the effort often involves trying to get as much information as possible from the received signals while rejecting as much unwanted signal energy ("noise") as possible.

One known and common method is often referred to as "harmonic imaging." As the name implies, instead of processing only the echo signal at the fundamental transmit frequency, this technique involves isolating and extracting information from one or more harmonics of this fundamental frequency either in addition to or instead of at the fundamental frequency alone. Such a technique is disclosed in:

U.S. Pat. No. 6,206,833;
U.S. Pat. No. 7,004,905;
U.S. Pat. No. 7,104,956; and
U.S. Pat. No. 7,513,870.

Echoes reflected from the ROI will typically include a linear component, which is associated with the ultrasonic pulses, and a nonlinear component, associated with the characteristic of tissues and structures of the body. The nonlinear component is extracted from the echoes, and the visible image is generated by processing and analyzing the nonlinear component.

One other known method for improving imaging quality is often referred to as "phase inversion" or "pulse inversion." This technique exploits the linearity of much of the medium through which the ultrasound pressure waves propagate through the ROI by transmitting and receiving a first ultrasound pulse, and then soon thereafter transmitting and receiving a second ultrasound pulse with a polarity opposite that of the first. Stated differently but equivalently, the two paired pulses differ in phase by 180 degrees. The combined (typically, summed) return signals will therefore "cancel" each other out (sum to zero) with respect to all linear propagation. The remaining signal is then either processed as is, or a harmonic of it is processed to create the displayed image (thereby using both the "phase inversion" and "harmonic imaging" techniques). U.S. Pat. Nos. 5,632,277 and 5,951,478 disclose examples of systems that use the "phase inversion" technique.

DETAILED DESCRIPTION

The following detailed description refers to the accompanying drawings. The same reference numbers may be used in different drawings to identify the same or similar elements. In the following description specific details may be set forth such as particular structures, techniques, etc. in order to provide a thorough understanding of the various aspects of the claimed invention. However, such details are provided for purposes of explanation and should not be viewed as limiting with respect to the claimed invention. With benefit of the present disclosure it will be apparent to those skilled in the art that the various aspects of the invention claimed may be practiced in other examples that depart from these specific details. Moreover, in certain instances, descriptions of well known devices, circuits, and methods are omitted so as not to obscure the description of the present invention with unnecessary detail.

Figure 1:
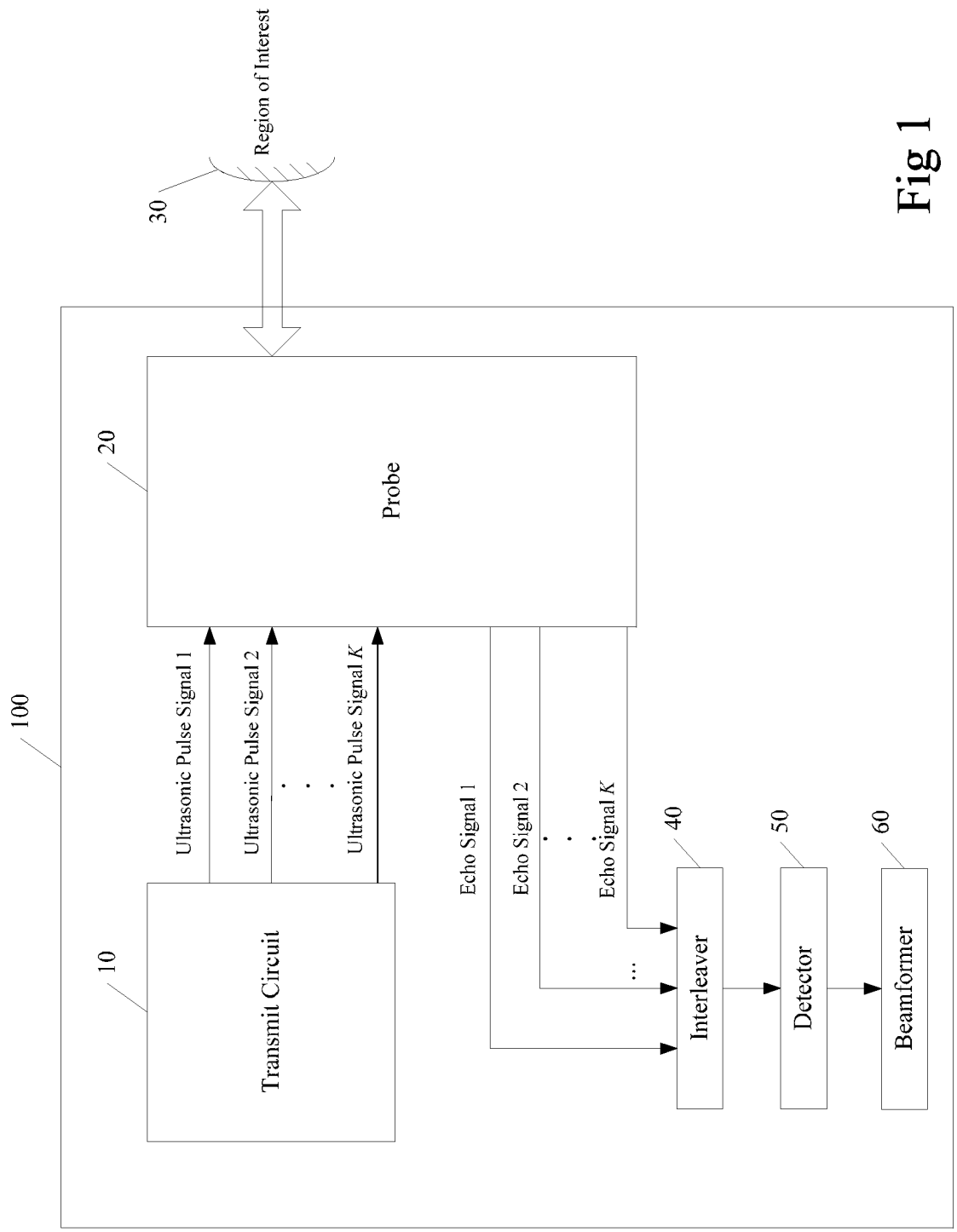
FIG. 1 is a block diagram of an offset pulse ultrasonic imaging system in accordance with an embodiment.

FIG. 1 shows a block diagram of an offset pulse ultrasonic imaging system 100 in accordance with an embodiment. As shown in FIG. 1, a transmit circuit 10 generates a plurality of ultrasonic pulse signals for each scan line in a scan plane. The plurality of ultrasonic pulse signals is converted into a plurality of ultrasonic pulses by a probe/transducer 20, which includes an array of piezoelectric elements. The structure and operation of an ultrasound probe/transducer are well understood and can be summarized by saying that it functions as a phased array of piezoelectric transmit/receive elements that generate and respond to pressure waves at ultrasonic frequencies. The ultrasonic pulses are offset relative to each other, which will be explained in detail later. The converted ultrasonic pulses are transmitted into a region of interest (ROI) 30 of a body. Since tissues of the body are nonlinear media, the echoes, reflected from the ROI 30, include a linear component associated with the ultrasonic pulses, and a nonlinear component associated with the characteristics of the various body tissues and other structures.

The ultrasound echoes reflected back from these body tissues and structures are then converted into echo signals by the probe 20. Conventional sampling, analog-to-digital and other circuitry is then used to convert the electrical signals created by the piezoelectric elements in the probe into a series of digital equivalent values, which are then supplied to an interleaver 40. As is explained in greater detail below, the interleaver 40 interleaves the values into a sequence of samples to form an operating signal. The operating signal is supplied to a detector 50. An explanation of the operating signal will be given in detail later. The nonlinear component of the is extracted from the operating signal in the detector 50 and is then beamformed in a beamformer 60 to generate a scan line, a collection of which is then converted in any know manner into a form suitable for display or recording or other processing by a user.

Figure 2:
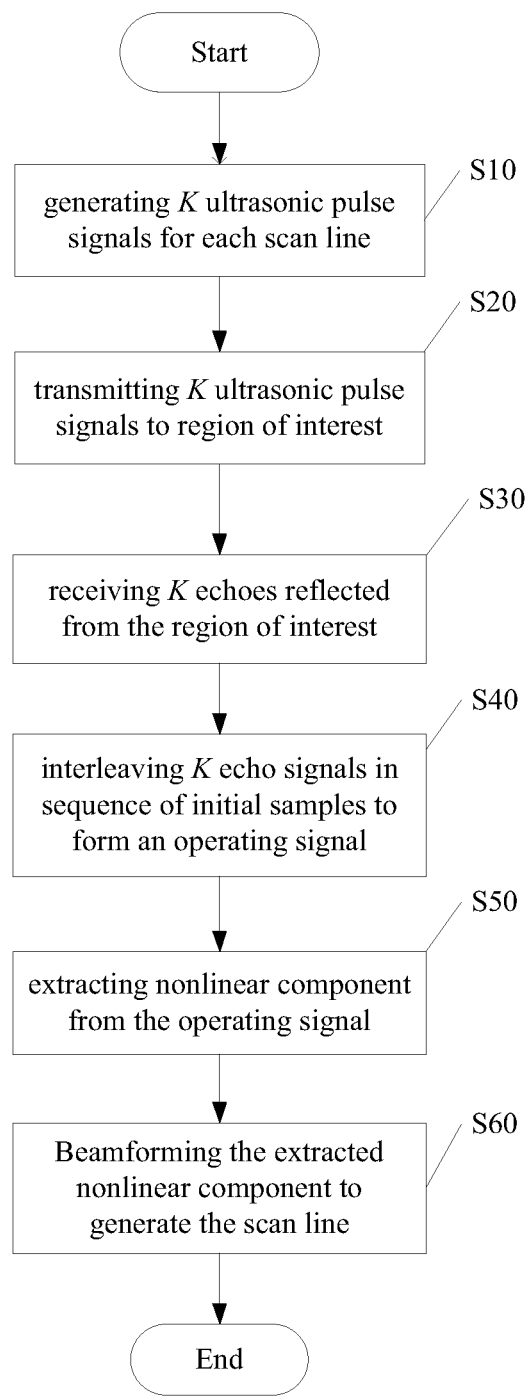
FIG. 2 is a flowchart of an offset pulse ultrasonic imaging method in accordance with an embodiment.

FIG. 2 is a flowchart of an offset pulse ultrasonic imaging method in accordance with an embodiment. In one embodiment, the method can be performed by the offset pulse ultrasonic imaging system 100 in FIG. 1.

First, at step S10, a transmit circuit 10 generates a plurality K of ultrasonic pulse signals for each scan line in a scan plane. That is, K ultrasonic pulse signals are emitted by the transmit circuit 10. For the K ultrasonic pulse signals, each ultrasonic pulse signal is time-shifted relative to an immediately preceding ultrasonic pulse signal by a predetermined amount. In one embodiment, the time-shift is $\tau=1/(K \cdot f_s)$ where $f_s$ is an initial sample rate for each scan line.

Each of the K ultrasonic pulse signals may optionally be weighted by a corresponding weight coefficient $$\cos\left(\frac{(k-1) \cdot 2\pi}{K} \cdot \alpha\right),$$

where K=1, 2 . . . K, and $\alpha$ is positive integer. If the $K^{th}$ ultrasonic pulse signal is represented by $P_K$, ultrasonic pulse signals $P_1, P_2, \ldots, P_K$ can be represented as:

$$P_1 = A(t)\sin(\omega t + \Phi_p)$$

$$P_2 = A(t+\tau)\cos\left(\frac{2\pi}{K} \cdot \alpha\right)\sin(\omega(t+\tau) + \Phi_p)$$

...

$$P_K = A(t+(k-1)\tau)\cos\left(\frac{(k-1) \cdot 2\pi}{K} \cdot \alpha\right)\sin(\omega(t+(k-1)\tau) + \Phi_p)$$

The absolute ratio of two weight coefficients represents the amplitude ratio of the two corresponding ultrasonic pulse signals. In the condition where the weight coefficient is positive, the waveform polarity of the corresponding ultrasonic pulse signal is positive; on the other hand, if the weight coefficient is negative, the polarity is negative.

At step S20, the K ultrasonic pulse signals are converted into K corresponding ultrasonic pulses by the probe 20, wherein each ultrasonic pulse is time-shifted relative to an immediately preceding ultrasonic pulse by the predetermined amount $\tau$. The K ultrasonic pulses are transmitted into the ROI 30 of the body. Because each of the K ultrasonic pulses is time-shifted relative to an immediately preceding ultrasonic pulse by $\tau$, the K ultrasonic pulses are relatively offset pulses emitted to the ROI 30.

Since many body tissues of interest comprise acoustically nonlinear media, the echoes, reflected from the ROI 30, include a linear component associated with the ultrasonic pulses and a nonlinear component associated with characteristics of tissues of the body. At step S30, the probe 20 receives K echoes and converts the K echoes into K echo signals. If the $K^{th}$ echo signal is represented by $E_K$, echo signals $$E_1 = A(t)\sin(\omega t + \Phi_e) + H(t)$$

$$E_2 = A(t+\tau)\cos\left(\frac{2\pi}{K} \cdot \alpha\right)\sin(\omega(t+\tau) + \Phi_e) + \cos^2\left(\frac{2\pi}{K} \cdot \alpha\right)H(t+\tau)$$

...

$$E_K = A(t+(k-1)\tau)\cos\left(\frac{(k-1) \cdot 2\pi}{K} \cdot \alpha\right)\sin(\omega(t+(k-1)\tau) + \Phi_e) +$$

$$\cos^2\left(\frac{(k-1) \cdot 2\pi}{K} \cdot \alpha\right)H(t+(k-1)\tau)$$

where H(t) represents the nonlinear component which carries information on characteristic of tissues of the body.

In this embodiment, K ultrasonic pulse signals are emitted by the transmit circuit 10 for each scan line in the scan plane associated with the initial sample rate $f_s$. The interleaver 40 thus may receive K echo signals converted by the probe 20 in the period of $\tau=1/f_s$. That is, in each sample interval of $1/f_s$, K echo signals ($E_1, E_2 \ldots E_K$) can be received by the interleaver 40. These echo signals ($E_1, E_2 \ldots E_K$) make up K samples in the sample interval of $1/f_s$.

Where the initial sample interval is $1/f_s$, the number of initial samples is N for each scan line in the scan plane. As mentioned above, there are K signals in the sample interval of $1/f_s$. The sampled values of the K signals in each sample interval of $1/f_s$ may then be interleaved in a sequence of the initial samples 1, 2 . . . N, to form the operating signal for generating the scan line, the number of current samples is N·K. If the operating signal is represented by W(t), W(t) may be made up of echo signals
$E_{11}$ $E_{12}$ . . . $E_{1K}$ $E_{21}$ $E_{22}$ . . . $E_{2K}$ . . . $E_{i1}$ $E_{i2}$ . . . $E_{ij}$ . . . $E_{iK}$ . . . $E_{N1}$ $E_{N2}$ . . . $E_{Nj}$ . . . $E_{NK}$,
i=1, 2 . . . N, j=1, 2 . . . K.

$$W(t) = A(t)\sin(\omega t + \Phi_e)\cos(2\pi\alpha f_s \cdot t) + H(t)\cos^2(2\pi\alpha f_s \cdot t) =$$

$$A(t)\sin(\omega t + \Phi_e)\cos(2\pi\alpha f_s \cdot t) + \frac{1}{2}H(t) + \frac{1}{2}H(t)\cos(4\pi\alpha f_s \cdot t)$$

Where $t = m\tau, m = 0, 1, 2 \ldots (N \cdot K - 1), \tau = 1/(Kf_s)$

The K echo signals are interleaved in the sequence of the initial samples (1, 2 . . . N) to form the operating signal W(t) in the interleaver 40. The operating signal W(t) is supplied to a detector 50 at step S40. Then, at step S50, the nonlinear component is extracted from the operating signal W(t) in the detector 50, and at step S60, the nonlinear component is beamformed in a beamformer 60 to generate the scan line. Since the nonlinear component carries information about characteristics of tissues of the body, a visible image of the ROI 30 is generated by analyzing the nonlinear component using known scan conversion and display algorithms.

It can be concluded from the expression of W(t): (1) the sample interval of the operating signal is $\tau$, so the effective sample rate of the operating signal is $K \cdot f_s$ which is K times the initial sample rate $f_s$; (2) the linear component of the operating signal is modulated to $\alpha$ times $f_s$, i.e. the linear component is moved to both sides of $\alpha \cdot f_s$ in the frequency domain; whereas, for the nonlinear component, half is not modulated and the other half is modulated to $2\alpha f_s$. That is, in the frequency domain, half of the nonlinear component is maintained at its original frequency and the other half is moved to both sides at $2 \cdot \alpha \cdot f_s$.

Detection of the nonlinear component at either side of $2 \cdot a \cdot f_s$ may avoid frequency overlap, or at least cause less overlap than in known methods. It is preferable to select $\alpha$ and K by considering the following equation. In accordance with Nyquist theorem:

$$KF_s \geq 2 \cdot \left(\frac{4\pi\alpha f_s}{2\pi}\right), \text{ i.e. } \frac{K}{\alpha} \geq 4$$

In this embodiment, each of the K ultrasonic pulse signals may be weighted by a corresponding weight coefficient, which causes the linear component to move to either side of $\alpha f_s$ in the frequency spectrum; as for the nonlinear component, half is maintained at the original fundamental frequency and the other half is moved to either side of $2\alpha f_s$. Accordingly, when the operating signal is analyzed in the detector 50, the nonlinear component is extracted efficiently because the linear component and the nonlinear component are separated in the frequency domain.

In another embodiment, the linear component may be overlapped by part of the nonlinear component (e.g. the nonlinear component moved to $2 \cdot a \cdot f_s$) in the frequency domain while the nonlinear component is maintained at the original fundamental frequency (i.e. non-modulated nonlinear component) instead of the nonlinear component being moved to both sides of $2\alpha f_s$ (i.e. modulated nonlinear component). The relevant information-bearing nonlinear signal component, can be extracted using known filtering methods provided that the non-modulated nonlinear component is sufficiently separated from the linear component and the non-modulated nonlinear component.

Figure 3:
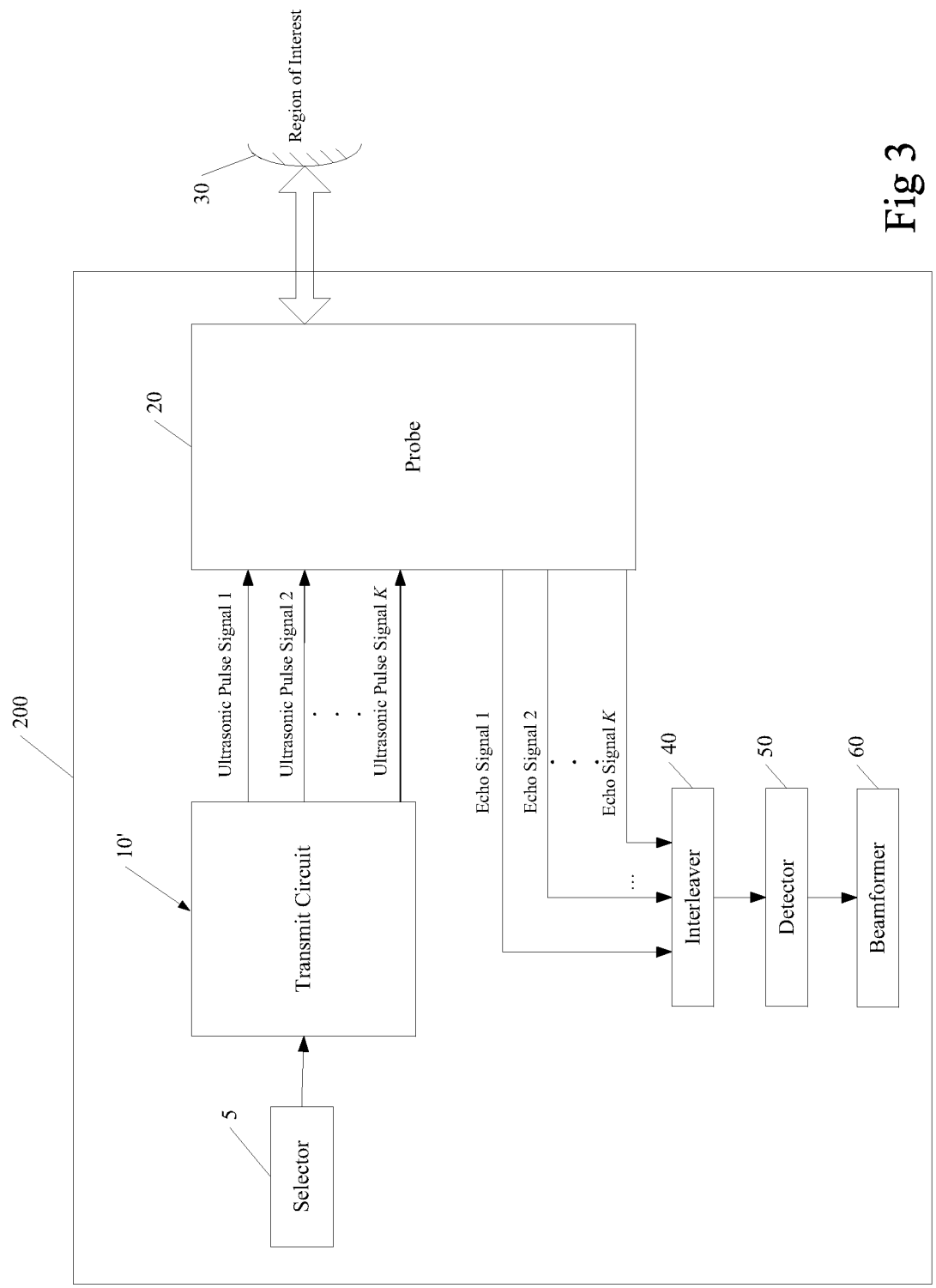
FIG. 3 is a block diagram of an offset pulse ultrasonic imaging system in accordance with another embodiment.

FIG. 3 shows a block diagram of an offset pulse ultrasonic imaging system 200 in accordance with another embodiment. As compared with the offset pulse ultrasonic imaging system 100, the system 200 further comprises a selector 5. The selector 5 may select suitable K and $\alpha$ for enabling the non-modulated nonlinear component to be separated from the linear component in the frequency domain and not be interfered with due to frequency overlap caused by the linear component and the modulated nonlinear component.

As shown in FIG. 3, a transmit circuit 10', based on the selected K and $\alpha$, generates a plurality of ultrasonic pulse signals for each scan line in a scan plane. The probe 20, interleaver 40, detector 50 and beamformer 60, can be implemented using the same or similar devices and programming as shown in FIG. 1.

Figure 4:
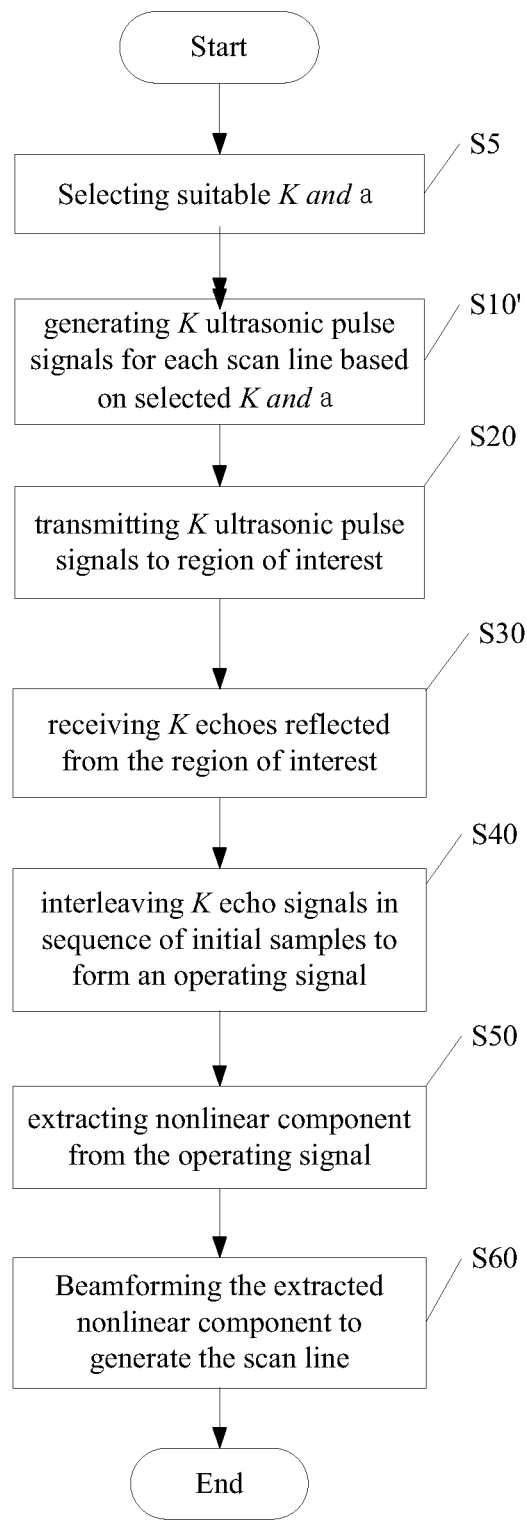
FIG. 4 is a flowchart of an offset pulse ultrasonic imaging method in accordance with another embodiment.

FIG. 4 is a flowchart of an offset pulse ultrasonic imaging method in accordance with an embodiment. In this embodiment, the method can be performed by the offset pulse ultrasonic imaging system 200 shown in FIG. 3. First, at step S5, a selector 5 selects suitable K and $\alpha$ values. The selected K and $\alpha$ may enable the non-modulated nonlinear component to be separated from the linear component, thereby reducing interference due to frequency overlap of the linear and nonlinear components in frequency domain. At step S10', a transmit circuit 10', based on the selected K and $\alpha$, generates a plurality of ultrasonic pulse signals, for example K, for each scan line in a scan plane. The following steps S20-S60 may be the same or similar as those shown in FIG. 2.

The system and the method as shown in FIG. 3 and FIG. 4 will be illustrated further by providing a group of particular values of K and $\alpha$. In one embodiment, K=2 and $\alpha$=1. In accordance with the expression for $P_K$ above, the ultrasonic pulse signals $P_1$ and $P_2$ can be represented as:

$$P_1 = A(t)\sin(\omega t + \Phi_p)$$
$$P_2 = A(t+\tau)\cos\left(\frac{2\pi}{K} \cdot \alpha\right)\sin(\omega(t+\tau) + \Phi_p) = -A(t+\tau)\sin(\omega(t+\tau) + \Phi_p)$$

Figure 5A:
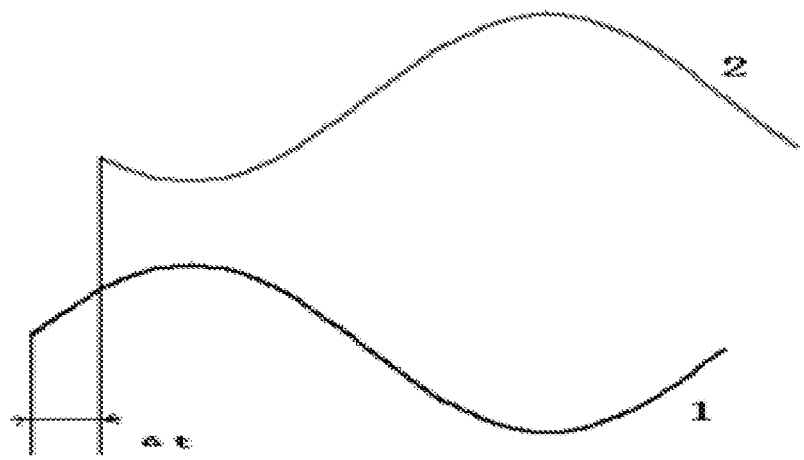
FIG. 5A-5D are graphs of waveforms for ultrasonic pulses and echoes in accordance with another embodiment.

In this example, the polarities of waveforms of ultrasonic pulse signals $P_1$ and $P_2$ are positive and negative respectively, and the amplitude ratio of $P_1$ and $P_2$ is 1:1. The ultrasonic pulse signal $P_2$ is time-shifted relative to the ultrasonic pulse signal $P_1$ by a predetermined amount $\tau=1/(2 f_s)$. The waveforms for the ultrasonic pulses $P_1$ and $P_2$ are illustrated in FIG. 5A.

The ultrasonic pulses $P_1$ and $P_2$ are transmitted into the ROI 30 and echo signals are reflected back to the transducer as usual. In accordance with the expression of echo signal $E_K$ above, the echo signals $E_1$ and $E_2$ can be represented as:

$$E_1 = A(t)\sin(\omega t + \Phi_e) + H(t)$$
$$E_2 = A(t+\tau)\cos\left(\frac{2\pi}{K} \cdot \alpha\right)\sin(\omega(t+\tau) + \Phi_e) + \cos^2\left(\frac{2\pi}{K} \cdot \alpha\right)H(t+\tau) =$$
$$-A(t+\tau)\sin(\omega(t+\tau) + \Phi_e) + H(t+\tau)$$

Figure 5B:
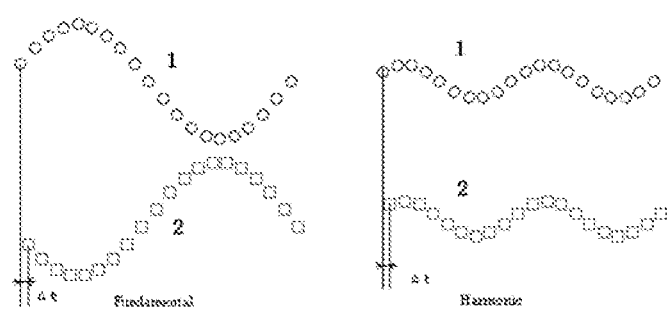

The waveforms for the echo signals $E_1$ and $E_2$ are illustrated in FIG. 5B, where the echo signal $E_1$ is illustrated with small circles and the echo signal $E_2$ is illustrated as small squares. The two echo signals $E_1$ and $E_2$ in each sample interval of $1/f_s$ are interleaved to form an operating signal W(t). In accordance with the expression of the operating signal W(t) as above mentioned, W(t) can be represented as:

$$W(t) = A(t)\sin(\omega t + \Phi_e)\cos(2\pi f_s \cdot t) + \frac{1}{2}H(t) + \frac{1}{2}H(t)\cos(4\pi f_s \cdot t)$$

In this embodiment, the sample rate of the nonlinear component is $2 f_s$ (K=2), so the operating signal W(t) can be further expressed as:

$$W(t) = A(t)\sin(\omega t + \Phi_e)\cos(2\pi f_s \cdot t) + H(t)$$

Figure 5C:
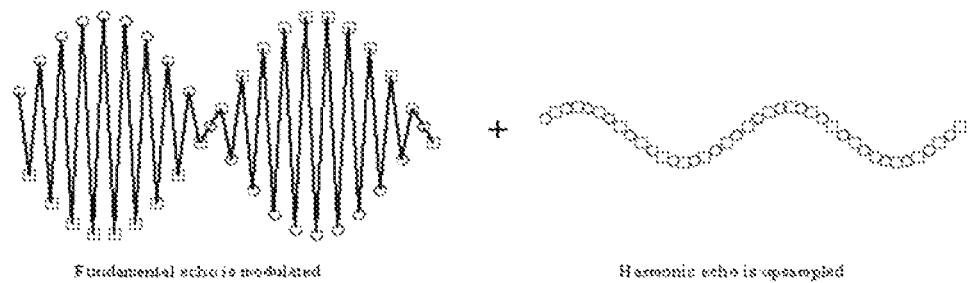
Figure 5D:
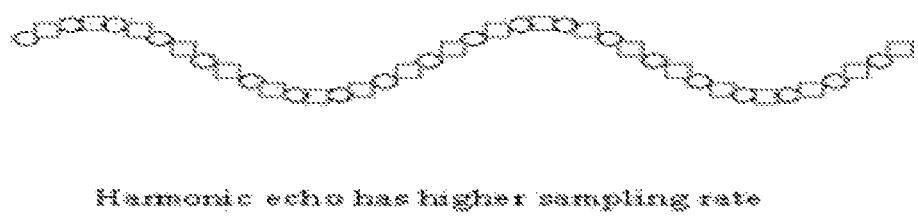

It can be concluded from the expression of W(t): (1) the sample rate of the operating signal is two times of the initial sample rate $f_s$, i.e. $2 \cdot f_s$, as shown in FIG. 5C, (2) the linear component is moved to either side of $f_s$ in frequency domain, the two central frequencies are located at $(f_s - \omega/2\pi)$ and at $(f_s + \omega 2\pi)$ respectively; and the nonlinear component is maintained at the fundamental frequency. Since the linear component and the nonlinear component are separated in the frequency domain, and the sample rate of the nonlinear component is two times the initial sample rate $f_s$, the linear component can be efficiently filtered using known filtering methods, for example, and the nonlinear component H(t) can be extracted efficiently as shown in FIG. 5D.

Figure 6A:
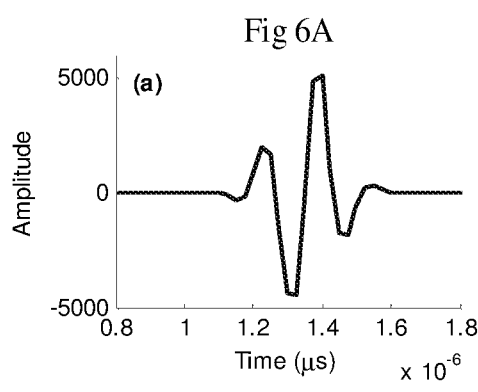
FIG. 6A-6D are graphs of echo waveforms at sample rates of 40 MHz, shown in a conventional ultrasonic imaging system and an ultrasonic imaging system in accordance with an embodiment respectively.
Figure 6B:
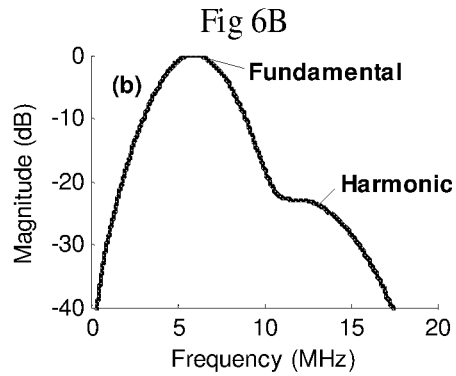
Figure 6C:
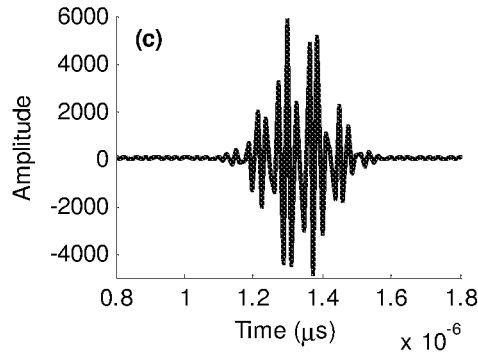
Figure 6D:
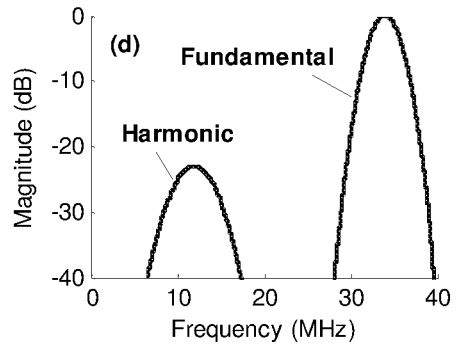

Further, in one illustrative embodiment, the initial sample rate $f_s$ is 40 MHz, the central frequency of the linear component is 6 MHz and the central frequency of the nonlinear component is 12 MHz. The waveforms of the operating signal W(t) are illustrated in FIG. 6C and FIG. 6D; whereas the waveforms of echoes in a conventional ultrasonic imaging system are shown in FIG. 6A and FIG. 6B. There will be significant frequency overlap in conventional ultrasonic imaging systems; however, according to the embodiment of the invention (K=2, α=1), not only the effective sample rate is increased to two times the initial sample rate $f_s$ (i.e. 80 MHz), but the linear component is much more completely separated from the nonlinear component in the frequency domain.

According to embodiments of the present invention, the sample rate of the nonlinear component is increased by virtue of the parameter K. Thus, almost all frequencies in the frequency band of the nonlinear component can be more efficiently detected even if the initial sample rate $f_s$ is not high.

Figure 7A:
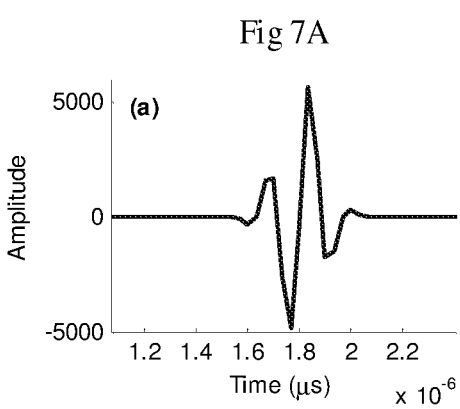
FIG. 7A-7D are graphs of echo waveforms at sample rates of 30 MHz, shown in a conventional ultrasonic imaging system and an ultrasonic imaging system in accordance with an embodiment respectively.
Figure 7B:
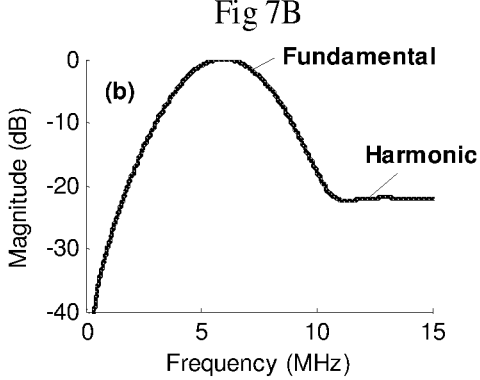
Figure 7C:
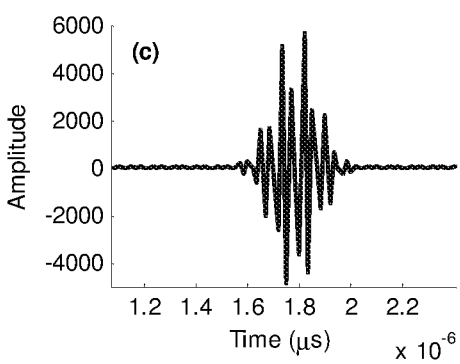
Figure 7D:
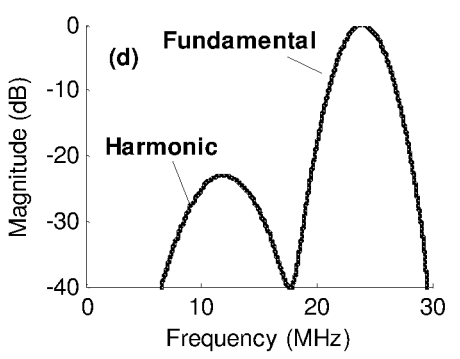

In another embodiment, the initial sample rate $f_s$ is 30 MHz. The waveforms of the operating signal W(t) are shown in FIG. 7C and FIG. 7D; the waveforms of echoes in a conventional ultrasonic imaging system are shown in FIG. 7A and FIG. 7B. As can be seen, because of significant frequency overlap in the conventional ultrasonic imaging system, the information at the frequencies in the frequency band of the nonlinear component cannot be detected completely; however, according to the embodiment of the present invention, not only the linear component can be separated from the nonlinear component in the frequency domain, but the sample rate can be increased to two times of the initial sample rate $f_s$ (in this example, 60 MHz), which enables almost all signal at frequencies in the frequency band of the nonlinear component to be much easier to isolate and detect.

Other groups of particular values of K and a can be selected. With the selected K and α, the effective sample rate of the operating signal is increased to K times the initial sample rate $f_s$, and the linear component is modulated to a location as far as possible from the nonlinear component in the frequency domain.

According to another illustrative embodiment, K=6, α=2, such that six ultrasonic pulse signals $P_1$, $P_2$ ... $P_6$ are generated for each scan line in the scan plane. The corresponding weight coefficients of the six ultrasonic pulse signals may then be 1, −½, −½, 1, −½, −½. The polarities of the waveforms for the six ultrasonic pulse signals are thus positive, negative, negative, positive, negative, negative, and the amplitude ratios of the six ultrasonic pulse signals are 1:0.5:0.5:1:0.5:0.5. For the six ultrasonic pulse signals, an ultrasonic pulse signal is time-shifted relative to an immediately preceding ultrasonic pulse signal by a predetermined amount $\tau=1/(2f_s)$.

The ultrasonic pulses $P_1$, $P_2$ ... $P_6$ are transmitted into the ROI 30, and the echoes reflected from the region 30 and sensed by the transducer as usual. The six echo signals $E_1$, $E_2$ ... $E_6$ are then interleaved in a sequence of initial samples to form an operating signal W(t). In accordance with the expression of the operating signal W(t) as above, W(t) can be represented:

$$W(t) = A(t)\sin(\omega t + \Phi_e)\cos(4\pi f_s \cdot t) + \frac{1}{2}H(t) + \frac{1}{2}H(t)\cos(8\pi f_s \cdot t)$$

It can be concluded from the expression of W(t): the linear component is moved to either side of $2 \cdot f_s$ in frequency domain; the two central frequencies are located at $(2f_s-\omega/2\pi)$ and $(2f_s+\omega/2\pi)$ respectively; for the nonlinear component, half of which is maintained at the original fundamental frequency and the other half of which is moved to either side of $4 \cdot f_s$; and the two central frequencies are located at $(4f_s-\omega/\pi)$ and $(4f_s+\omega/\pi)$. In this embodiment, the effective sampling rate of the operating signal is increased to six times the initial sampling rate, that is, to $6 \cdot f_s$ (K=6). Due to the interference of frequency overlap, within an active range of $0 \sim 3f_s$ for frequency detection, the linear component, which is moved to both sides of $2 \cdot f_s$, is overlapped or partly overlapped with the nonlinear component, which is moved to both sides of $4f_s$ ($-4f_s+6f_s=2f_s$) at $2 \cdot f_s$ in the frequency domain. However, the other half of the nonlinear component, which is maintained at original fundamental frequency, is not significantly affected by the frequency overlap. Since half of the nonlinear component, which is maintained at original frequency, is separated from the linear component, which is moved to either side of $2 \cdot f_s$ in the frequency domain, and the half of the nonlinear component, which is maintained at original frequency, is not interfered with significantly by the frequency overlap, the linear component can be filtered out using conventional filtering methods and the nonlinear component H(t) can be extracted from the operating signal W(t).

In an ultrasonic imaging system according to embodiments of the invention, K ultrasonic pulse signals are emitted into a region of interest of a body for each scan line in a scan plane. Accordingly, K echoes are reflected by the region of interest. An operating signal is formed by interleaving K echoes signals. When the operating signal is detected to extract the information from the nonlinear component of the echoes, the frequency of the linear component of the echoes is modulated away so as to enable more efficient separation from the nonlinear component in frequency domain.

The offset pulse ultrasonic imaging system and method thereof should not be limited to embodiments mentioned above. It will be apparent to those skilled in the art that the various aspects of the invention claimed may be practiced in other examples that depart from these specific details.

In an alternative embodiment of the ultrasonic imaging method, a plurality of groups of ultrasonic pulses are transmitted into a region of interest of a body for each scan line in a scan plane, wherein each group of ultrasonic pulses comprises K ultrasonic pulses. For example, a transmit circuit may generate three groups of ultrasonic pulses for each scan line in a scan plane, each group of ultrasonic pulses comprising two ultrasonic pulses $P_1$ and $P_2$, wherein $P_2$ is time-shifted relative to $P_1$ by a predetermined amount, and the two ultrasonic pulses $P_1$ and $P_2$ are optionally weighted by corresponding weight coefficients. The predetermined amount and the corresponding weight coefficients may adopt parameters disclosed in above embodiments. The three groups of ultrasonic pulses ($P_1$, $P_2$, $P_1$, $P_2$, $P_1$, $P_2$) are emitted into the region of interest. The echoes reflected from the region of interest are received by the probe/transducer as usual. The received echoes accordingly include six echo signals ($E_1$, $E_2$, $E_1$, $E_2$, $E_1$, $E_2$). Each group of echo signals ($E_1$, $E_2$ pair) is interleaved in a sequence of initial samples to form an operating signal associated with the group of echo signals. Therefore, three groups of echo signals ($E_1$, $E_2$ pairs) are interleaved to form three operating signals $W_1$, $W_2$, $W_3$. The nonlinear component associated with each of the groups of echo signals is then extracted from the corresponding operating signal; that is, nonlinear components $h_1$, $h_2$ and $h_3$ are extracted from $W_1$, $W_2$, $W_3$ respectively. In a module such as the detector in above embodiments, the extracted nonlinear components $h_1$, $h_2$ and $h_3$ can be combined, for example, as a resultant of the extracted nonlinear components, by summing the nonlinear components, i.e. $H=h_1+h_2+h_3$. The SNR (signal-to-noise ratio) of H may thereby be improved in comparison with the SNR of each of linear components $h_1$, $h_2$ and $h_3$.

In addition, the selector described above may be configured to allow for user adjustment. The selector may select suitable K and α values based on the active range of frequency detection. With the selected K and α, a transmit circuit generates K ultrasonic pulse signals for each scan line in a scan plane. In an alternative embodiment, a particular transmit circuit may generate a predetermined plurality of ultrasonic pulse signals for each scan line in a scan plane.

Further, as in other embodiments, the amplitude of each of the K ultrasonic pulse signals may be weighted by a corresponding weight coefficient. In an alternative embodiment, K ultrasonic pulse signals are emitted to a region of interest of a body for each scan line in a scan plane, wherein the amplitude of each of the K ultrasonic pulse signals is not weighted. K echoes are reflected by the region of interest accordingly. An operating signal is formed by interleaving K echoes signals. When the operating signal is detected to extract nonlinear component of the echoes, the effective sampling rate of the operating signal is increased to K times the initial sample rate $f_s$. Since the linear component is not modulated, the linear component may be overlapped with the nonlinear component in the frequency domain. A narrow-band filter that passes narrowband ultrasonic pulse signals may then be used to extract the nonlinear component in this embodiment.

Also, an ultrasonic pulse signal is time-shifted relative to an immediately preceding ultrasonic pulse signal by a predetermined amount. In some of the above-mentioned embodiments, the time-shift $\tau=1/(K\cdot f_s)$ wherein $f_s$ is the initial sample rate for each scan line. In an alternative embodiment, the time-shift τ may be set another predetermined value, for example, $1/(2\cdot K\cdot f_s)$. Correspondingly, some modifications might be made to the ultrasonic imaging system. For example, a synchronizer may be added into the system as needed to keep the ultrasonic pulse signals emitted by the transmit circuit and the received echoes synchronized so as to form an operating signal.

FIGS. 8-11 illustrate in a different and perhaps more visible way the two-pulse embodiment of the invention described above. The illustrated example also shows the principle of the invention in terms of phase shift instead of time shift, although these two representations are of course equivalent mathematically. In the illustrated example, two transmit pulses P1(t) and P2(t) are shown in greatly simplified form for the sake of clarity; all skilled in medical ultrasound engineering realize that actual transmit pulses from a modern ultrasound imaging transducer— especially with the usual multi-element phased piezoelectric array— may have a much more complicated waveform.

Figure 8:
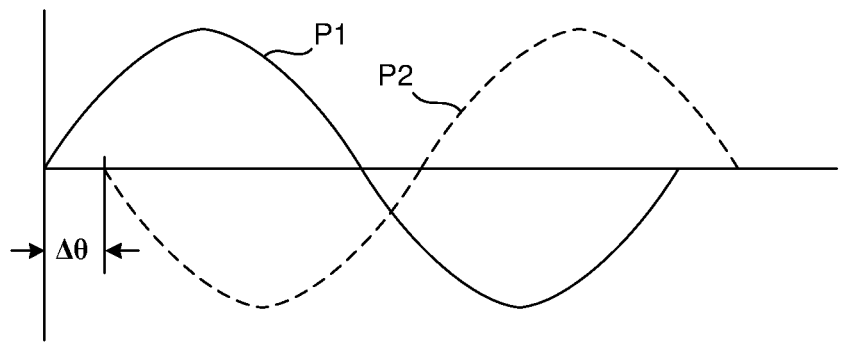
FIG. 8 illustrates a two-pulse embodiment and how a second pulse is offset from a first.

The main point to be illustrated in FIG. 8 is that the second pulse in the series is generated so as to be offset in phase from P1 by Δθ, which is neither 0 degrees nor 180 degrees. In other words, in this invention, the second pulse P2 is not just a "repeat" (0° phase shift or a multiple of 360°) of the first pulse P1, nor is it the "inverse" (180° phase shift or a multiple thereof) of P1, but is rather offset from P1 by an amount that is other than 0° or 180°.

Figure 9A:
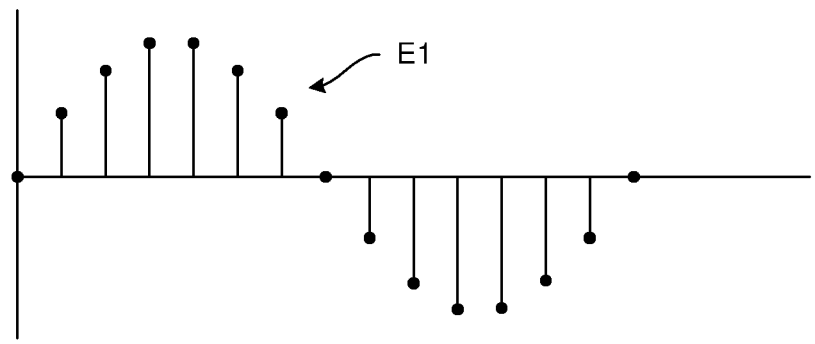
FIGS. 9A and 9B illustrate how the pulses shown in FIG. 8 may be discretized.
Figure 9B:
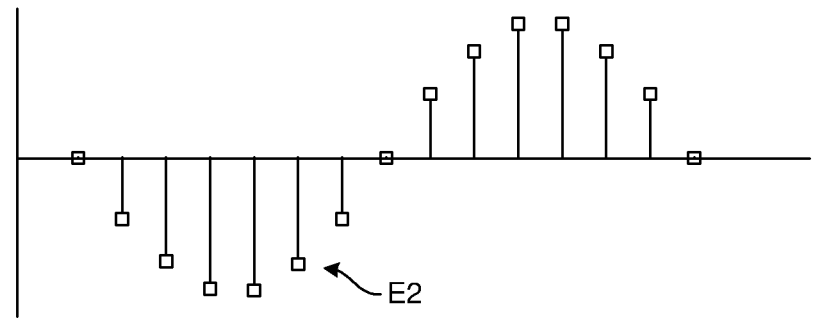
Figure 10:
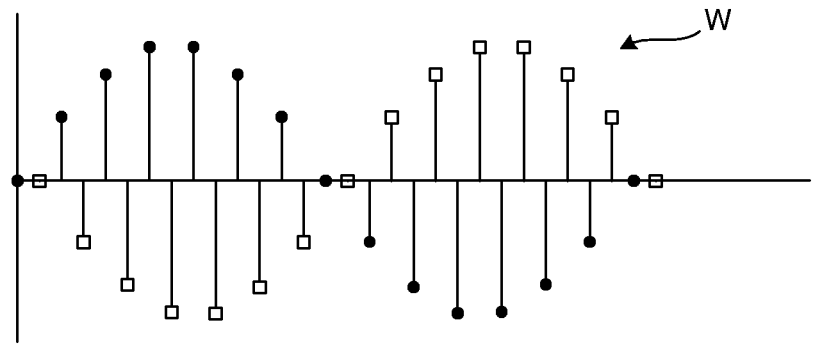
FIG. 10 illustrates echo pulse interleaving.

Sampling of analog signals to generate corresponding numerical representations is of course a well-known feature of almost all digital signal processing. In FIGS. 9A and 9B, receive/echo signals E1, E2 corresponding to transmit pulses P1, P2, respectively, are illustrated in discretized form, such that $E1=E1(i)$, $i=0, 1, \ldots$ and $E2=E2(j)$, $j=0, 1, \ldots$ FIG. 10 illustrates graphically how E1 and E2 may be interleaved such that the values $E2(j)$ are aligned "in between" temporally adjacent values of $E1(i)$. If P2 is sampled at the same frequency as P1, then each $E2(j)$ value can be interleaved temporally in the middle of the adjacent $E1(i)$ values. The combined, that is, interleaved resultant operating signal W will thereby have twice as many values per cycle as either E1 or E2 alone; in other words, the effective sampling rate of the interleaved resultant signal is twice the actual sampling rate used to discretize each of the return signals from P1 and P2. The combined, interleaved operating signal W can then be processed as if it were a single discretized receive signal Those skilled in the art will readily see how the two-pulse embodiment illustrated in FIGS. 8-10 can be extended to even more pulses with suitable relative offsets. In other words, although FIGS. 8-10 illustrate an example with K=2, the principle can be extended to embodiments in which K>2.

Figure 11:
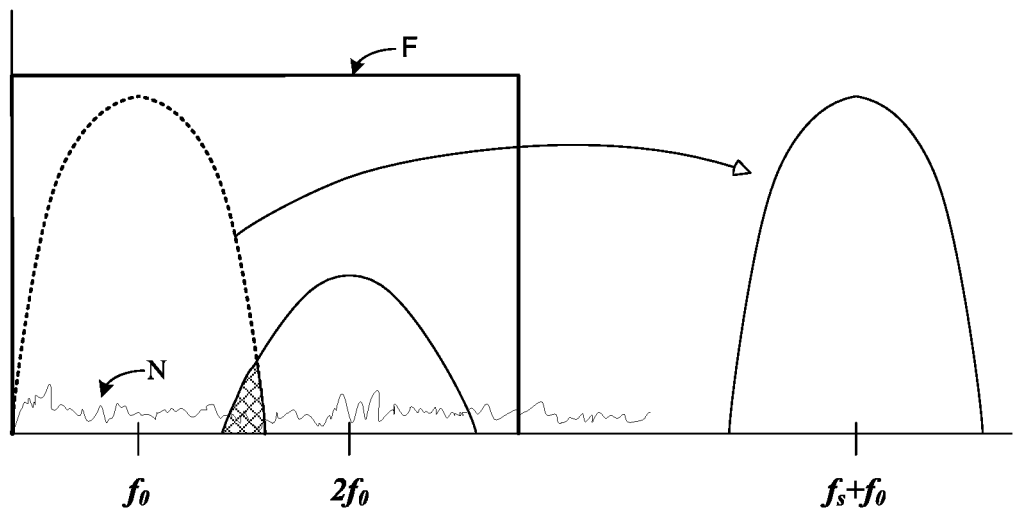
FIG. 11 illustrates how pulse offsetting and interleaving affect the spectrum of receive signals.

FIG. 11 illustrates the effect of transmit pulse offsetting and receive pulse interleaving. Assume first that there were no such offsetting and interleaving. The spectral component at the fundamental frequency $f_0$ (shown with the dashed line) and the spectral component at the first harmonic (centered on $2f_0$) will overlap (shown with hatched shading); moreover, even a narrow-band filter will typically also pass energy from the fundamental component in addition to the harmonic information, noise, and non-linear information N. One prior art way to try to overcome this inherent problem is to then try to extract even higher-order harmonic information, but as is well known, the amplitude of such higher-order harmonics becomes lower and lower, thereby making it more and more difficult to maintain a good signal-to-noise ratio.

The effect of transmit pulse offsetting and return signal interleaving and compounding is that the spectral component at the fundamental frequency $f_0$ is shifted both upward and downward relative to the origin, with the positive shift (illustrated by the arrow arc from the dashed $f_0$ "curve" to the solid $f_s+f_0$ curve). One advantage of this is that a band-pass filter narrowly tuned to the harmonic $2f_0$ is not necessary; rather, even a broader-spectrum filter F can suffice; alternatively, the signal from a band-pass filter will not be as degraded by component overlap.

The amount of offset, that is, Δθ may be adjusted according to the needs of any given implementation of the invention and could even be made user-adjustable during scans to find a "best" image result. In general, as Δθ increases, the degree of separation, that is, fundamental component up-shift, will increase, but accuracy will decrease. For K=2, a suitable value for Δθ will typically be $\Delta\theta=(f_s/2f_0)(1/360)$.

What is claimed is:

1. A method for creating an image of a region of interest of a body comprising:
   transmitting K ultrasonic pulses into the region of interest, wherein K is at least 2;
   sensing K receive signals corresponding to ultrasonic energy from the K ultrasonic pulses reflected from within the region of interest;
   interleaving discretized representations of the K receive signals to form a resultant operating signal; and creating the image of the region of interest as a function of the resultant operating signal;

wherein each successive ultrasonic pulse of the K ultrasonic pulses is phase-shifted relative to an immediately preceding ultrasonic pulse by an amount other than zero degrees or a multiple of 180 degrees, and wherein:

the amount that each successive ultrasonic pulse is phase-shifted is chosen such that each successive ultrasonic pulse is transmitted with a time delay of $1/K \cdot f_s$; and the K receive signals are discretized with an initial sampling rate of $f_s$.

2. The method of claim 1, further comprising:

extracting a nonlinear component from the operating signal; and beamforming the nonlinear component to generate a scan line, whereby a series of scan lines form the image.

3. The method of claim 2, further comprising frequency filtering the operating signal using a filter than passes not only a frequency that is a harmonic of a fundamental signal frequency, but also energy at the fundamental signal frequency itself.

4. The method of claim 1, wherein amplitudes of the K ultrasonic pulses are weighted by corresponding weight coefficients.

5. The method of claim 4, wherein the weight coefficient for the amplitude of a $k^{th}$ ultrasonic pulse is $$\cos\left(\frac{2\pi(k-1)}{K} \cdot \alpha\right), k = 1, 2 \ldots K,$$

$\alpha$ is positive integer and the center frequency of the linear component is moved to $\alpha f_s$.

6. The method of claim 5, wherein the (K, $\alpha$) is selected from any one of groups of (2, 1) and (6, 2).

7. A system for creating an image of a region of interest of a body comprising:

an ultrasound transducer configured to transmit K ultrasonic pulses into the region of interest, the ultrasound transducer sensing K receive signals corresponding to ultrasonic energy from the K ultrasonic pulses, respectively, from within the region of interest, wherein K is at least 2;

transmit control circuitry configured to cause the ultrasound transducer to phase-shift each successive ultrasonic pulse of the K ultrasonic pulses relative to an immediately preceding ultrasonic pulse by an amount other than zero degrees or a multiple of 180 degrees, wherein:

the amount that each successive ultrasonic pulse is phase-shifted is chosen such that each successive ultrasonic pulse is transmitted with a time delay of $1/K \cdot f_s$; and the K receive signals are discretized with an initial sampling rate of $f_s$;

an interleaver configured to interleave discretized representations of the K receive signals to form a resultant operating signal; and detection and beamforming circuitry configured to create the image as a function of the resultant operating signal.

8. The system of claim 7, in which the detection and beamforming circuitry comprises:

a detector configured to extract a nonlinear component from the operating signal for each group of ultrasonic pulses and to generate a resultant of the nonlinear component for each group of transmitted ultrasonic pulses; and a beamformer configured to beamform the resultant of the nonlinear component for each group of ultrasonic pulses to generate a scan line, whereby a series of scan lines form the image.

9. The system of claim 7, wherein amplitudes of the K ultrasonic pulses are weighted by corresponding weight coefficients.

10. The system of claim 9, wherein the weight coefficient for the amplitude of a $k^{th}$ ultrasonic pulse is $$\cos\left(\frac{2\pi(k-1)}{K} \cdot \alpha\right), k = 1, 2 \ldots K,$$

$\alpha$ is positive integer and the center frequency of the linear component is moved to $\alpha f_s$.

* * * * *